United States Patent [19]

Krenitsky

[11] 4,219,621

[45] Aug. 26, 1980

[54] STABILIZED THYMIDINE PHOSPHORYLASE PREPARATION AND CULTURE MEDIUM

[75] Inventor: Thomas A. Krenitsky, Chapel Hill, N.C.

[73] Assignee: Burroughs Wellcome Co., Research Triangle Park, N.C.

[21] Appl. No.: 915,153

[22] Filed: Jun. 13, 1978

[30] Foreign Application Priority Data

Jun. 14, 1977 [GB] United Kingdom .............. 24665/77

[51] Int. Cl.$^2$ .......................... C12Q 1/18; C12N 9/12; C12N 1/20

[52] U.S. Cl. ..................................... 435/32; 435/194; 435/253

[58] Field of Search ................... 195/63, 99, 100, 101, 195/102, 103; 435/32, 193, 33, 253, 243, 194

[56] References Cited

U.S. PATENT DOCUMENTS 4,097,337  6/1978  Krenitsky et al. .................. 195/100

*Primary Examiner*—Robert J. Warden
*Attorney, Agent, or Firm*—Donald Brown

[57] ABSTRACT

Thymidine phosphorylase counteracts antagonists to antifolate agents in media used for testing the susceptibility of bacteria to anti-folate antimicrobial agents. A solution of thymidine phosphorylase may be stabilized by addition of inorganic phosphate and uracil, the stabilization being most effective at pH7. Furthermore, bovine serum albumin is added to prevent loss of enzymic activity on filtration. The solution may be kept sterile by addition of sodium or potassium azide.

25 Claims, No Drawings

STABILIZED THYMIDINE PHOSPHORYLASE PREPARATION AND CULTURE MEDIUM

This invention relates to a preparation of thymidine phosphorylase for incorporation into culture media used for the testing of the susceptibility of bacteria to anti-folate anti-microbial agents such as sulphamethoxazole (SMX) and/or trimethoprim (TMP), in particular it relates to an improved stabilised thymidine phosphorylase preparation.

It has been known for a number of years that culture media in common use are often unsuitable for determining sensitivity of bacteria to sulphonamides or trimethoprim, that is, agents interfering with the synthesis of folates in these organisms. This unsuitability manifests itself by giving long tailing end-points when the serial dilution method is used, and by partial growth within the inhibition zones when the diffusion method is employed. It has been shown by Bushby, *Med. J. Aust. Special Supplement*, 1973, 1, 10 and Kock and Burchall, *Applied Microbiology*, 1971, 22, 812 that thymidine is a very potent reversing agent of the inhibiting activities of sulphonamides and trimethoprim.

In 1945 Harper and Cawston, *J. Path. Bact.*, 57, 59, showed that when lysed horse blood was added to a poor susceptibility test medium, it could convert it into a satisfactory one. Since this early work, and that of several other workers, it has become common practice to include lysed horse blood in antibacterial susceptibility test media, in order to reduce the partial growth often observed within the inhibition zones produced by sulphonamides. More recently this method has also been shown to be similarly effective in testing with respect to trimethoprim (Bushby, *Postgraduate Med. J.*, 1969, 45, 10; and Darrell et al., *J. Clin. Path.*, 1968, 21, 202).

Harper and Cawston established that the lysed horse blood contained a factor which neutralises sulphonamide-antagonising substances, and that this so-called Harper-Cawston Factor is effective only with media which contain a moderate level of thymidine, that is from about 0.1 to 15 µg/ml. Below about 0.1 µg/ml, the activity of the drugs is not antagonised, and in this way, removal of such a small amount of thymidine has no effect on the drug inhibition observed. At very high levels of thymidine, that is greater than about 15 µg/ml, the activity of the Harper-Cawston Factor is not sufficient to overcome the reversal of the activities of the sulphonamides and trimethoprim, possibly because the high concentration of thymine produced as a result of the cleavage of thymidine, can replace the much more active thymidine in the reversal.

The Harper-Cawston Factor has been reported to be thymidine phosphorylase (Bushby in *Trimethoprim/Sulphamethoxazole* in Bacterial Infections: A Wellcome Foundation Symposium Ed. Bernstein & Salter, Churchill Livingston, Edinburg & London, 1973, 1, 10–18; Ferone et al, *Antimicrobial Agents and Chemotheraphy*, (1975), 7, 91). It has been pointed out in the former reference that "although thymidine interferes with the in vitro activity of trimethoprim/sulphamethoxazole, it is not usually present in animals in sufficiently high concentrations to affect the in vivo activity".

The disadvantages of including lysed horse blood in a culture medium are that it imparts a reddish brown colour to the medium and that the requirement of its addition to bacterial culture media means that the media are virtually impossible to define. A further disadvantage of using sterile horse blood is that it is commercially available in very limited supply and from only a very few suppliers world-wide.

It is already established that the addition of the isolated and purified enzyme thymidine phosphorylase of bacterial origin to a wide variety of commonly used growth media, those media for susceptibility testing of bacteria to anti-folate drugs, as is disclosed in copending British Patent Application No. 3445/75. The practical use of the enzyme, however, is limited by the forms in which it has been known to be stable. It is known from the prior art that solutions of thymidine phosphorylase of bacterial origin are stable at −20° C. but at 4° C. activity decreases at a significant rate (Schwartz, *Eur. J. Biochem.*, (1971), 21, 191). Thus, in order to overcome this difficulty the aforementioned patent application describes stable formulations of the enzyme which comprise of either ammonium sulphate suspensions or concentrated, but not dilute solutions (>5 mg protein/ml) of the enzyme in 10% ammonium sulphate. There are, however, a number of disadvantages associated with these types of formulation. For instance, the suspensions settle rapidly, are difficult to aliquot quantitatively and are also difficult to sterilise without denaturing the enzyme since filtration methods cannot be used. The concentrated solutions of the enzyme in 10% ammonium sulphate are disadvantageous not only because of their cost and the danger of microbial contamination by multiuse packaging but also because at concentrations under which reasonable stability is achieved (~2,000 I.U./ml), 1 ml. of the enzyme will treat approximately 100 litres of media. For these reasons it was desirable to discover conditions under which this enzyme was stable in dilute as well as concentrated solution.

A kinetic analysis of thymidine phosphorylase purified from *Escherichia coli* suggested that under certain conditions thymine, phosphate, and thymidine phosphorylase may form a dead-end complex, that is a complex which is itself not catalytically active but the formation of which must be reversed before the enzyme can form catalytically active complexes. This finding suggested that the dead-end complex might be more stable than the free enzyme. Since thymine is an undesirable additive to the media; as hereinabove explained, a substitute for this was looked for.

It has now been found that a combination of uracil and inorganic phosphate, for example potassium phosphate, is a very effective stabiliser of thymidine phosphorylase in both concentrated and dilute solutions.

According to one aspect of the invention there is provided a stabilised thymidine phosphorylase preparation containing uracil and inorganic phosphate.

The thymidine phosphorylase for use in the present invention may be obtained by purification from a number of bacteria such as *Salmonella typhimurium*, *Bacillus cereus*, *Bacillus stearothermophilus*, *Haemophilus influenzae* and particularly from a strain of *Escherichia coli* requiring thymine and methionine for growth. The purification may be carried out by the method described by Schwartz, *Eur., J. Biochem*, (1971), 21, 191–198, which method involves a somewhat lengthy process of precipitation, fractionation, chromatography and dialysis. A more preferred process is that described in copending British Patent Application No. 3445/75 which application discloses that a certain strain of *E. coli*, produces inordinate amounts of thymidine phosphorylase under appropriate growth conditions and that it may be isolated and purified by applying the cell extract to specific adsorbents and eluting it therefrom, to give a much higher yield and purity than the method of Schwartz.

Monitoring of the eluates at all stages of the purification process employed may be carried out using a spectrophotometric assay at a selected wavelength in order to ascertain enzyme activity which is expressed in International Units (I.U.), one International Unit being equivalent to that amount of enzyme that will phosphorylise one micromole of thymidine to thymine under the assay conditions used (see Example 1). The peaks that show the highest concentration and purity are selected.

The enzyme so purified as above is then made available, as previously stated, in a stable form by addition of a combination of uracil and inorganic phosphate. Although a variety of phosphate salts can be used, potassium or ammonium phosphate are preferred.

The concentration of thymidine phosphorylase incorporated into the media is preferably in the range of about 0.01 to 1,000 International Units/ml and more preferably between 0.01 to 10 International Units/ml.

The useful concentration limits for uracil and phosphate to produce a stabilised thymidine phosphorylase preparation are 0.5 mM to saturation, preferably 1 to 20 mM, for uracil, and 0.1 mM to saturation, preferably 0.1 to 1.0 M for the inorganic phosphate.

In certain cases, filtration of the enzyme formulation will result in loss of enzyme activity. It has been found however, that addition of serum albumin, for instance, bovine serum albumin, overcame this difficulty.

According to a further aspect of the present invention there is provided a stabilised thymidine phosphorylase preparation containing uracil and phosphate to which serum albumin is added to prevent loss of enzyme activity by filtration.

The serum albumin is preferably added at a concentration of 0.1 to 5%.

The sterility of the above described formulations is of great importance in view of their application to the testing of the sensitivities of bacteria to antifolates. It is often desirable, therefore, to add an antimicrobial agent to the formulation in order to ensure sterility. It is important however that the antimicrobials employed are able to sterilise the formulation without affecting the enzyme stability. It has been found that alkali metal azides such as sodium azide or potassium azide are excellent antimicrobials for the purposes of the present invention since they do not interfere with enzyme activity and in the use of the formulations of the present invention are diluted out to ineffectiveness as antimicrobial agents.

According to yet another aspect of the present invention there is provided a sterile stabilised thymidine phosphorylase preparation containing a combination of uracil and phosphate and an antimicrobial agent which is capable of sterilising the said preparation without affecting the enzyme stability.

The antimicrobial agent, as hereinabove defined, may be incorporated into the preparation at a concentration of 0.001 to 0.4%, preferably 0.002 to 0.2%.

It has further been found that the stability of thymidine phosphorylase in the preparation has hereinbefore described is a function of the pH, the greatest stability being achieved in the range of pH 6 to pH 8, most preferably pH 7.

Formulations of thymidine phosphorylase prepared in the manner of the present invention make possible the facile sterile packaging of amounts of enzyme which are within the realm of practicality for use in media treatment in individual diagnostic laboratories.

The following examples illustrate the invention but are not intended to limit it in any way:

EXAMPLE 1

An experiment was performed to investigate the stability of thymidine phosphorylase preparations containing various initial concentrations of enzyme which had been purified from *E. coli* and stabilised with ammonium sulphate. Each enyzme solution contained ammonium sulphate (700 mM), potassium phosphate buffer (83 mM), and bovine serum albumin (2.5%) at pH 6.8. Enzyme activity was monitored at 25° C. and 290 nm ($\Delta E = 1000 M^{-1} cm^{-1}$) & at 200 mM potassium phosphate, pH 7.4, and 1 mM thymidine. The following results were obtained:

| Thymidine Phosphorylase (Initial I.U. /ml) | % of Original Activity After 110 days at 5° C. |
|---|---|
| 1300 | 98 |
| 400 | 90 |
| 40 | 79 |
| 4 | 40 |
| 0.4 | 3 |

As can be seen from the above, this formulation, according to copending U.K. application No. 3445/75, effectively stabilises thymidine phosphorylase preparation only at relatively high concentrations of the enzyme.

EXAMPLE 2

An experiment was performed to investigate the stability of thymidine phosphorylase preparation purified from *E. coli* in dilute solution (1.5 I.U./ml) and either left unstabilised or stabilised with various combinations of uracil and phosphate and uracil or phosphate alone at various pH values. Each solution also contained bovine serum albumin (2.5%) and sodium azide (0.02%). Again, enzyme activity was monitored as in Example 1. The following results were obtained:

| Stabilizers Added | % of Original Activity* After 32 days at 37° C. | | |
|---|---|---|---|
| | pH 6 | pH 7 | pH 8 |
| None | 0 | 0 | 0.6 |
| 500mM Phosphate | 43 | 72 | 70 |
| 17.5mM Uracil | 19 | 1 | 0.9 |
| 17.5mM Uracil and 500mM Phosphate | 100 | 100 | 93 |
| 0.5mM Uracil and 500 mM Phosphate | — | 85 | — |

* = 1.5 I.U./ml

As can be seen from the above, uracil alone or potassium phosphate alone are not as effective in stabilising the enzyme as is their combination. Furthermore, this combination is much more effective with low concentrations of enzyme than is the formulation used in Example 1.

I claim:

1. A thymidine phosphorylase preparation characterised in that the preparation also comprises uracil and an inorganic phosphate.

2. A preparation as claimed in claim 1 characterised in that the inorganic phosphate is present in the concentration range 0.1 mM to saturation.

3. A preparation as claimed in claim 2 characterised in that the inorganic phosphate is present in the concentration range 0.1 M to 1.0 M.

4. A preparation as claimed in claim 1, 2 or 3 characterised in that the inorganic phosphate is potassium phosphate.

5. A preparation as claimed in claims 1, 2 or 3 characterised in that the uracil is present in the concentration range 0.5 mM to saturation.

6. A preparation as claimed in claim 1, 2, or 3 characterised in that the uracil is present in the concentration range 1 mM to 20 mM.

7. A preparation as claimed in claim 1 characterised in that the preparation also comprises serum albumin.

8. A preparation as claimed in claim 7 characterised in that the serum albumin is bovine serum albumin.

9. A prepraration as claimed in claim 7 characterised in that the serum albumin is present in the concentration range 0.2 to 5%.

10. A preparation as claimed in claim 1 characterised in that the preparation also comprises an antimicrobial agent.

11. A preparation as claimed in claim 10 characterised in that the antimicrobial agent is an alkali metal azide.

12. A preparation as claimed in claim 11 characterised in that the alkali metal azide is present in the concentration range 0.001 to 0.4%.

13. A preparation as claimed in claim 12 characterised in that the alkali metal azide is present in the concentration range 0.002 to 0.2%.

14. A preparation as claimed in claim 10 characterised in that the antimicrobial agent is sodium azide.

15. A preparation as claimed in claim 10 characterised in that the antimicrobial agent is potassium axide.

16. A preparation as claimed in claim 1 characterised in that the pH of the preparation is in the range pH 6 to pH 8.

17. A preparation as claimed in claim 16 characterised in that the pH of the preparation is pH 7.

18. A preparation as claimed in claim 1 characterised in that the preparation is enclosed in a sterile package.

19. A culture medium for testing the susceptibility of bacteria to anti-folate anti-microbial agents characterised in that a preparation of thymidine phosphorylase as claimed in claim 1, is incorporated in the medium.

20. A culture medium as claimed in claim 19 characterised in that the thymidine phosphorylase is present in the concentration range 0.01–1000 International Unit/ml.

21. A culture medium as claimed in claim 20 characterised in that the thymidine phosphorylase is present in the concentration range 0.02–10 International Units/ml.

22. A preparation according to claim 1 in which the inorganic phosphate is present in the concentration range 0.1 mM saturation and the uracil is present in the concentration range of 0.5 mM to saturation.

23. The preparation according to claim 22 in which the pH of the preparation is 6 to 8.

24. The preparation according to claim 22 in which the pH of the preparation is 6 to 8 and the concentration of thymidine phosphorylase in the preparation is 0.01 to 1,000 International Units/ml.

25. The preparation according to claim 24 in which the inorganic phosphate is potassium phosphate or ammonium phosphate.

* * * * *